US008540656B1

(12) United States Patent
Powlan (10) Patent No.: US 8,540,656 B1
(45) Date of Patent: Sep. 24, 2013

(54) APPARATUS AND METHOD FOR THE TREATMENT OF FRACTURES OF THE DISTAL RADIUS

(76) Inventor: Roy Y. Powlan, Lafayette, CA (US)

( * ) Notice: Subject to any disclaimer, the term of this patent is extended or adjusted under 35 U.S.C. 154(b) by 0 days.

(21) Appl. No.: 13/374,982

(22) Filed: Jan. 26, 2012

(51) Int. Cl.
*A61F 5/00* (2006.01)

(52) U.S. Cl.
USPC .................................. 602/36; 602/32; 602/40

(58) Field of Classification Search
USPC ................. 602/32, 33, 34, 35, 36, 38, 39, 40;
482/10, 62, 69; 128/845–846, 877, 878,
128/879, 880, 897, 898; 5/621–624, 635,
5/647; 606/241
See application file for complete search history.

(56) References Cited

U.S. PATENT DOCUMENTS

| 2,243,294 | A | 4/1941 | Steams |
| 2,584,203 | A | 2/1952 | Hart |
| 2,590,739 | A | 3/1952 | Wagner |
| 2,783,758 | A | 3/1957 | Trott |
| 3,087,489 | A | 4/1963 | Gilbert |
| 3,693,617 | A | 9/1972 | Trott |
| 3,850,166 | A | 11/1974 | Tamny |
| 4,445,506 | A | 5/1984 | Johansson |
| 5,074,291 | A | 12/1991 | Carter |
| 5,441,480 | A | 8/1995 | Kane |
| 6,758,827 | B2 | 7/2004 | Moss |
| 6,811,541 | B2 * | 11/2004 | Lambert ........................ 602/36 |
| 7,131,955 | B2 | 11/2006 | Price |
| 2006/0200061 | A1 | 9/2006 | Warkentine |
| 2010/0069809 | A1 | 3/2010 | Sommers |

OTHER PUBLICATIONS

S.A. Earnshaw,Closed reduction of Colles Fractures;Comparison Manual & Finger traps. Journal Bone & Joint Surgery, Mar. 2002, 84 A;354-8.

* cited by examiner

*Primary Examiner* — Patricia Bianco
*Assistant Examiner* — Ophelia A Hawthorne (57) ABSTRACT

An apparatus and method for the treatment of fractures of the distal radius having a means for applying traction to a fractured forearm using a resilient cantilever spring digit gripping device to assist in the manipulative reduction of the fracture, and a means for maintaining the reduced fracture of the distal forearm in a determinable position of flexion, ulnar deviation and pronation enabling the application of a closely fitting, well molded immobilization means such as a cast.

6 Claims, 5 Drawing Sheets

APPARATUS AND METHOD FOR THE TREATMENT OF FRACTURES OF THE DISTAL RADIUS

BACKGROUND

Prior Art

The following is a tabulation of some prior art that presently appears to be relevant:

U.S. PATENTS

| Pat. No. | Kind Code | Issue Date | Patentee |
| --- | --- | --- | --- |
| U.S. Pat. No. 2,590,739 | B1 | Mar. 25, 1952 | Wagner |
| US 2006/0200061 | A1 | Published Sep. 07, 2006 | Warkentine |
| U.S. Pat. No. 2,584,203 | B1 | Feb. 05, 1952 | Hart |
| U.S. Pat. No. 3,850,166 | B1 | Nov. 26, 1974 | Tamny |
| U.S. Pat. No. 4,445,506 | B1 | Apr. 01, 1984 | Johansson |
| U.S. Pat. No. 5,074,291 | B1 | Dec. 24, 1991 | Carter |
| U.S. Pat. No. 5,441,480 | B1 | Aug. 15, 1995 | Kane |
| U.S. Pat. No. 6,758,827 | B1 | Jul. 06, 2004 | Moss |
| U.S. Pat. No. 3,087,489 | B1 | Apr. 30, 1963 | Gilbert |
| U.S. Pat. No. 2,243,294 | B1 | Apr. 27, 1941 | Stearns |
| U.S. Pat. No. 2,783,758 | B1 | Mar. 05, 1957 | Trott |
| U.S. Pat. No. 3,693,617 | B1 | Sep. 26, 1972 | Trott |
| U.S. Pat. No. 7,131,955 | B1 | Nov. 07, 2006 | Price |
| US 2010/0069809 | A1 | Published Mar. 18, 2010 | Sommers |

NON-PATENT LITERATURE DOCUMENTS

Closed Reduction of Colles Factures: Comparison of Manual Manipulation and Finger Trap Traction. S. A. Earnshaw et al., American Journal of Bone and Joint Surgery, 2002, March 84A, P. 354-358.

FIELD OF THE INVENTION

This invention relates to an apparatus that provides safe, quickly applied traction to a fractured forearm, enabling an efficient reduction of the fracture. It then maintains the reduced fracture in the most desirable position for stability as determined by the surgeon, so that a well molded, closely fitted padded cast can be applied to maintain the position, thereby reducing the tendency of the fractured fragments to re-displace.

BACKGROUND OF THE INVENTION

Fractures of the distal radius, also known as Colles fractures, are usually the result of a fall on the out-stretched hand. The force and the direction of the fall most often causes the distal end of the radius bone to break off and become angled backwards and displaced away from the midline, often impacted and comminuted, with an obvious shortening of the forearm. While some of the more severe displaced fractures require open surgery, many can be effectively treated with closed reduction by manipulation, followed by cast immobilization.

Most closed reduction and casting is usually done in one of two ways, the first being manual traction and manipulation with one, or preferably two assistants, one to maintain traction, and the other to prepare the casting materials while the surgeon holds the fractured fragments in place with one hand during which she applies the padding and cast with the other, sometimes resulting in a badly constructed cast that fails to hold the fractured bones in place properly. Additionally, the assistant supporting the arm often flexes the wrist excessively causing the distal fragment to tilt dorsally.

The second method employs mechanical assistance to provide traction, usually with Chinese finger traps suspended from a standard, sometimes with a rope, pulleys and weights to provide traction, and with counter-traction above the flexed elbow. While this method lessens the reliance on an assistant, it still has disadvantages. The wire finger traps can cut into the skin of the fingers, often requiring them to be first wrapped with tape for protection, after which the traps must also be over-wrapped with tape to prevent them from sliding off the fingers when traction is applied. This is a tedious and time consuming procedure when several fingers and the thumb need to be wrapped, and tourniquet and anesthesia time is limited. In addition, straight traction using finger traps tends to pull the wrist out straight, making it difficult to cast the wrist and forearm in flexion and ulnar deviation. The quandary is well illustrated in an article by: Earnshaw, Journal of Bone and Joint Surgery, Vol. 84A, #3, which analyses 225 Colles fractures.

It is generally recognized that the positioning of the forearm within the cast is critically important if slipping and re-displacement of the fractured fragments is to be avoided. Ideally, while the cast is being applied, the forearm should be in traction, with the wrist deviated towards the ulnar side, and with the forearm in pronation, with the palm facing downwards. Most importantly, the cast should provide padded pressure over the dorsal surface of the distal radial fragment combined with padded pressure over the opposite volar surface of the distal radius proximal to the fracture, which in effect, results in slight flexion of the wrist, and prevents re-displacement of the distal radial fragment.

Because of the difficulty of meeting the exacting requirements of the closed reduction, positioning and casting of these difficult fractures, many inventions have attempted to overcome these problems, but none have proven to be universally successful. The present invention avoids the use of finger traps and provides an adjustable and comfortable traction means, easily and quickly applied and removed, that enables reduction and casting of the fracture without the need for assistants. Following reduction, the forearm can be placed into a position of optimal stability and maintained in this position, leaving the surgeon's hands free to apply a closely fitting, well-padded cast, molded in such a way as to minimize any tendency of the fracture fragments to re-displace.

The prior art does not disclose a finger gripping device comprising soft digital grips and long cantilever springs, resulting in a comfortable grip on the fingers and thumb, with the range of grip on the fingers varied by means of a ratchet, nor does the prior art disclose an adjustable support arm that enables ulnar deviation, nor a means for supination and pronation of the wrist in combination with a rope and pulley traction means, nor does the prior art disclose a means for providing adjustable pressure over the volar surface of the distal radial shaft with resulting wrist flexion, yet not interfering with proper cast application.

The following is some relevant prior art relating to the treatment of fractures of the distal radius.
U.S. Pat. No. 2,590,739, (1952) Wagner, describes an apparatus for upper arm and forearm traction only, mainly for fractures of the humerus. It consists of a strap and sling placed around the wrist and suspended from an over-head frame.

Counter-traction is provided by a strap placed above the flexed elbow. There is no provision for any positioning other than traction on the forearm.

U.S. Patent application No. US 2006/0200061 A1, (2006) Warkentine, describes a forearm operating table providing traction only, with a wrist strap similar to Wagner, or with finger traps, but with an added crank device to increase traction. Again, there is no provision for the positioning of the fractured fragments and with the forearm fastened down to a table, cast application would be very difficult.

U.S. Pat. No. 2,584,203 (1952) to Hart, describes a forearm traction device providing traction only, using rubber tubes instead of finger traps because, "The usual finger traps cause trauma to the tissues-" Counter-traction is provided by a bracket above the flexed elbow.

U.S. Pat. No. 3,850,166 (1974) Tamny et al, describes a fracture reduction system essentially similar to Hart, but employing the usual finger traps. In addition to traction, it provides variable spacing between the fingers and thumb, as well as a means for supination and pronation of the forearm. It provides straight in-line traction only, by means of a screw adjustment, making it difficult to achieve flexion and ulnar deviation of the wrist while applying a cast.

U.S. Pat. No. 4,445,506 (1984) Johansson, describes the use of straight finger trap traction, employing a traction tower, with counter-traction provided by a sling over a flexed elbow. There is no provision for positioning the forearm in flexion, ulnar deviation, or pronation, other than in traction, which is varied by a crank device.

U.S. Pat. No. 5,074,291 (1991) Carter; U.S. Pat. No. 5,441,480 (1995) Kane; and U.S. Pat. No. 6,758,827 (2004) Moss; describe the use of finger traps for digital traction in conjunction with hand operating tables. Again, there is no provision for positioning the forearm other than placing it in traction.

U.S. Pat. No. 3,087,489 (1963) Gilbert, describes a universal orthopedic traction and holding device, for the leg and upper arm as well as the forearm. When employed for the forearm, it provides straight traction to the fingers with counter-traction applied to above the flexed elbow. Instead of finger traps, the fingers are flexed around a bar and held in this way while traction is applied through the bar to the middle row of phalanges. The bar can be rotated for supination or pronation, but there is no provision for flexion or ulnar deviation, and the straight traction makes it difficult to achieve those positions for casting.

U.S. Pat. No. 2,243,294 (1938) Stearns, describes a forearm traction tower with a finger gripping device other than finger traps. The finger gripping device consists of narrow elongated box, open top and bottom, that encases the base of the fingers, excluding the thumb, with rubber blocks between the base of the fingers. Clamps at either end of the box compress the base of the fingers together, while a bale attached to the ends of the box provides traction. It is apparent however, that since the rubber blocks are not attached to the box, the entire device would tend to slide off the fingers with minimal traction. Since the thumb is not included in the traction device, ulnar deviation is limited. The provision to achieve flexion of the wrist by rotating the box around its long axis, would result only in flexion of the metacarpal-phalangeal joints of the fingers, not of the wrist.

U.S. Pat. No. 2,783,758 (1957), Trott, and U.S. Pat. No. 3,693,617 (1972) Trott, describe a traction tower, from which the forearm is suspended by a single finger trap placed on the thumb. Counter-traction is provided by a weight placed above the flexed elbow, and is described as 5 pounds equaling to a pull of 15 pounds on the finger trap on the thumb and is said to provide ulnar deviation as well as traction. A single finger trap used to provide full traction alone could cause severe damage to the skin, and could possibly dislocate the metacarpal-phalangeal joint. An arm support section is employed to press against the mid-forearm to provide flexion of the wrist, which would interfere with the proper application and molding of a cast, and if incorporated in the cast, could lead to pressure sores.

U.S. Pat. No. 7,131,955 (2006) Price, describes a traction tower system consisting of a frame that grips the elbow at its base, and suspends the fingers rigidly, not including the thumb, from an upright part of the frame by means of the usual finger traps. The amount of traction is determined by adjusting the height of the upright, an ineffective method, because once adjusted, even a slight movement of the elbow or of the fracture, during manipulation would change the amount of traction drastically, requiring constant re-adjustment. Also, the lack of thumb traction limits the ability to achieve ulnar deviation. An "adjustable joint" in the upright, is said to "enable a user to apply the tractive forces selectively to the patient's wrist in different positions by placing the adjustable joint at substantially at the same height as the wrist," "to allow for flexion, extension, radial deviation or ulnar deviation of the wrist." In actual practice however, the raising or lowering of the adjustable joint of the tower to correspond to the level of the wrist, or the angling of the tower in any direction, merely changes the direction of traction between the elbow and fingers, or between the fingers and the encircling brace around the upper part of the forearm, and would have limited if any effect on the disposition of the fractured fragments, or the amount of angular deviation of the wrist. Additionally, the presence of the supporting bracket and strap around the upper forearm makes it difficult to apply a properly fitting cast, and if removed prior to casting, all of the positioning of the fracture is lost.

Pub. No. US 2010/0069809 A1 (2010) Sommers et al, describes an attempt to correct one of the short-comings of Price described above i.e. the inability of the device to maintain a constant traction force. Sommers describes the placement of constant force springs between the finger traps and the top of the tower, which still does not correct the short-comings of Price, since the spring range is limited, making manipulation difficult.

SUMMARY OF THE INVENTION

In accordance with one embodiment, an apparatus and method for the treatment of distal radial fractures comprises a traction tower with means for providing traction to a fractured forearm, through the use of pulleys and weights, with counter-traction being supplied by a sling above the elbow in the usual manner. The application of the traction to the forearm, however, is accomplished by an apparatus that eliminates the use of finger traps and rigid finger clamps. The apparatus employs long adjustable resilient cantilever spring blades with softly padded arc-like finger grips at their tips which grip the fingers at their base and provide a quickly and easily applied and removed means for applying traction. A separate but basically similar device provides traction to the thumb.

In addition to providing traction, the apparatus is able to hold the forearm and hand in the position of flexion, deviated towards the ulnar side, pronation and flexion, positions generally considered to be optimal for stability of the fractured bones within the cast. The apparatus is able to maintain these positions, leaving the surgeons both hands free to apply a properly padded, closely fitted cast, thereby maximizing the ability of the fracture to heal without further displacement.

ADVANTAGES

The advantages of this wrist fracture apparatus are as follows:
1. It enables the surgeon to treat a fractured radius without the need for one or more assistants, and also enables a less skilled operator as well, to obtain optimal results.
2. It employs the usual time-tested traction tower with pulleys and weights for an easily changed amount of traction, depending on the size and anatomy of the patient, while enabling the freedom of motion of the arm necessary while it is being manipulated. It also maintains a constant amount of traction before, during, and after manipulation.
3. It avoids the use of skin damaging finger traps, and their tedious application and removal. Instead, it uses a comfortable, easily and quickly applied and removed finger gripping means.
4. It applies traction to the thumb with an outrigger arm, as well as to the fingers, thereby enabling ulnar deviation. The use of separate thumb traction creates a space for the cast to continue between the thumb and the adjacent fingers resulting in better immobilization.
5. It is easily adaptable for right or left forearm injuries, and for large or small hands.
6. It provides a means for applying desirable diffuse pressure over the distal volar shaft of the radius, which in combination of pressure over the dorsal surface of the distal end of the radius with a well-padded and molded cast, helps prevent backward displacement of the distal fragment, and in doing so, does not interfere with the application of a proper cast, as does some of the prior art.
6. It provides a means for positioning the forearm in any degree of supination or pronation, as desired by the surgeon, and maintains the set position while the cast is being applied.
7. All of these features combined into one easy to use apparatus, enable the surgeon to efficiently prepare the patient and reduce the fractured fragments back into place. After the reduction of the fracture has taken place, the apparatus then holds the forearm in the position best suited for stability of the fracture, including traction, flexion, ulnar deviation and pronation, freeing the surgeon's hands for the application of a well-fitted, well molded cast to the arm with padded pressure over critical areas to hold the bones in their proper position. As a result of the fracture being well reduced into as stable a position as possible, and able to be maintained in this position by a closely molded cast, a greater percentage of this type of fracture are more likely to heal without further displacement that would necessitate further surgery by the surgeon,
8. It has been estimated that there are approximately 300,000 wrist fractures in the US each year. More of these fractures being successfully treated by closed means rather than by open surgery would result in great savings medically, as well as economically.

DETAILED DESCRIPTION OF THE DRAWINGS

Figure 1:
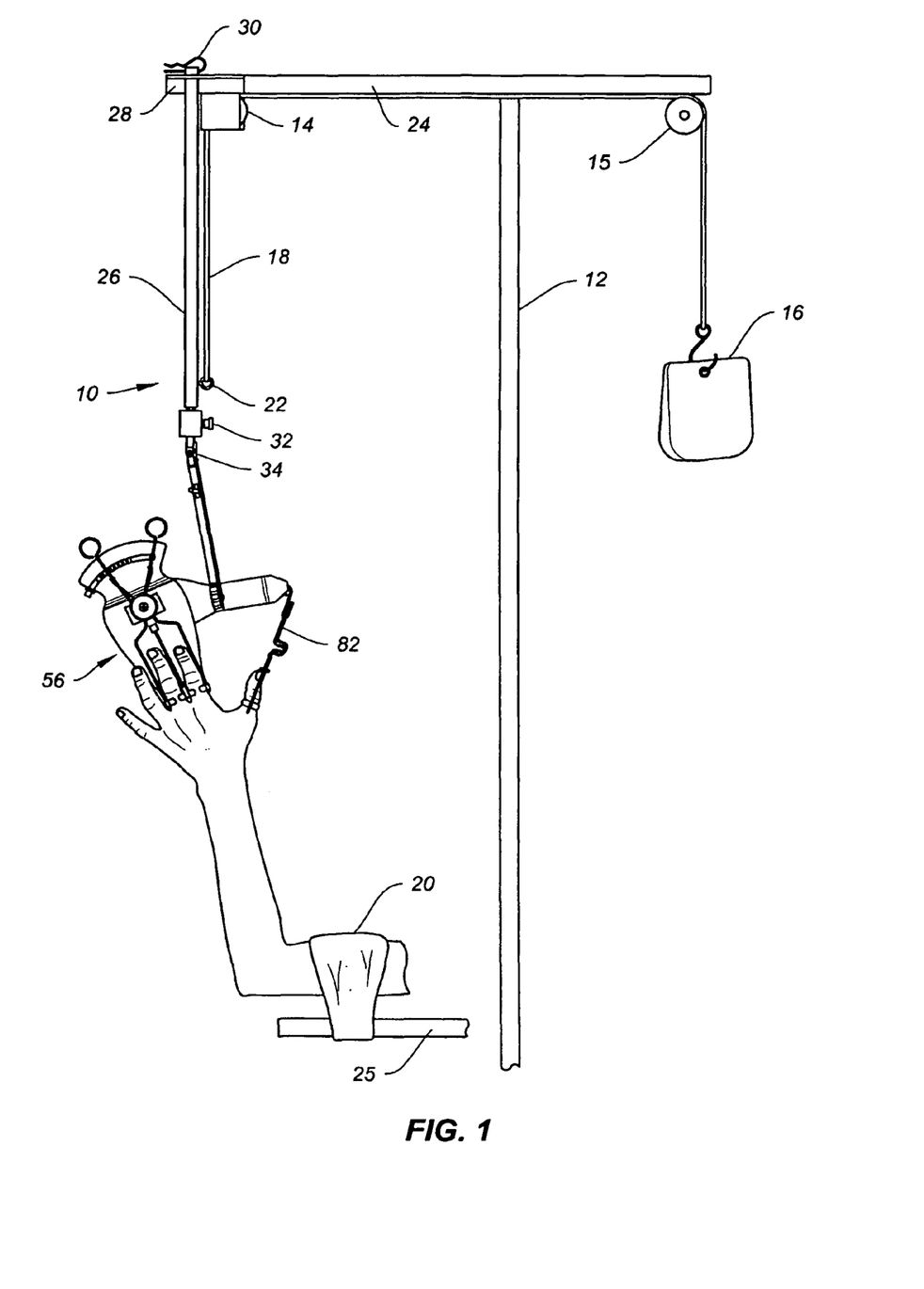
FIG. 1 is an orthogonal view of a hand and forearm in traction with the complete fracture apparatus suspended from a support assembly.

FIG. 1 illustrates the complete distal radius fracture apparatus 10 suspended from a support assembly 12 with a support bar 24 at its upper end and two pulleys 14 and 15, and a variable weight 16, and an elongate flexible suspension means 18, in this embodiment, a rope or cable. This method of applying traction is preferable to some prior art that uses springs because during manipulation of the wrist needed to achieve reduction of the fracture, it is necessary to have a wide range of motion of the fractured wrist in order to manipulate the fractured bones back into position. The elbow is fixed with a cuff 20 to a support bar 25 for counter-traction.

Traction is applied to the fracture apparatus 10 by means of an elongate flexible suspension means 18 and by means of an eyelet, 22, which is fastened to the base of an elongate rotation control rod, 26, which in one embodiment has a square cross section.

The purpose of the square cross section of the rotation control rod 26, is to allow it to slide up and down in the square opening 100 (shown in FIG. 6) of the pulley bracket 28, during manipulation of the fracture, and to prevent it from rotating in the opening 100 after the desired degree of pronation has been selected. Swivel 32 and universal joint 34 enable the elongate adjustable suspension arm 36, the finger gripping device 56 and the thumb traction device 82 to rotate relative to the rotation control rod 26.

A hairpin cotter pin 30 limits the translation of the rotation control rod 26 in the bracket 28.

Figure 6:
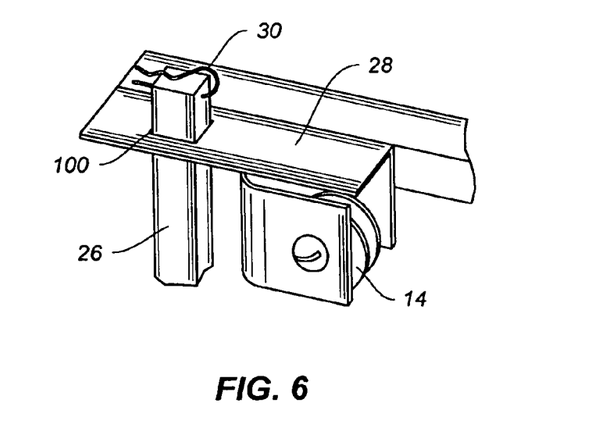
FIG. 6 is a view of the pulley bracket with a pulley and an opening for the square rotation control rod.

The rotation control rod 26 and opening 100, could be of any cross section other than round, that would limit rotation.

Figure 2:
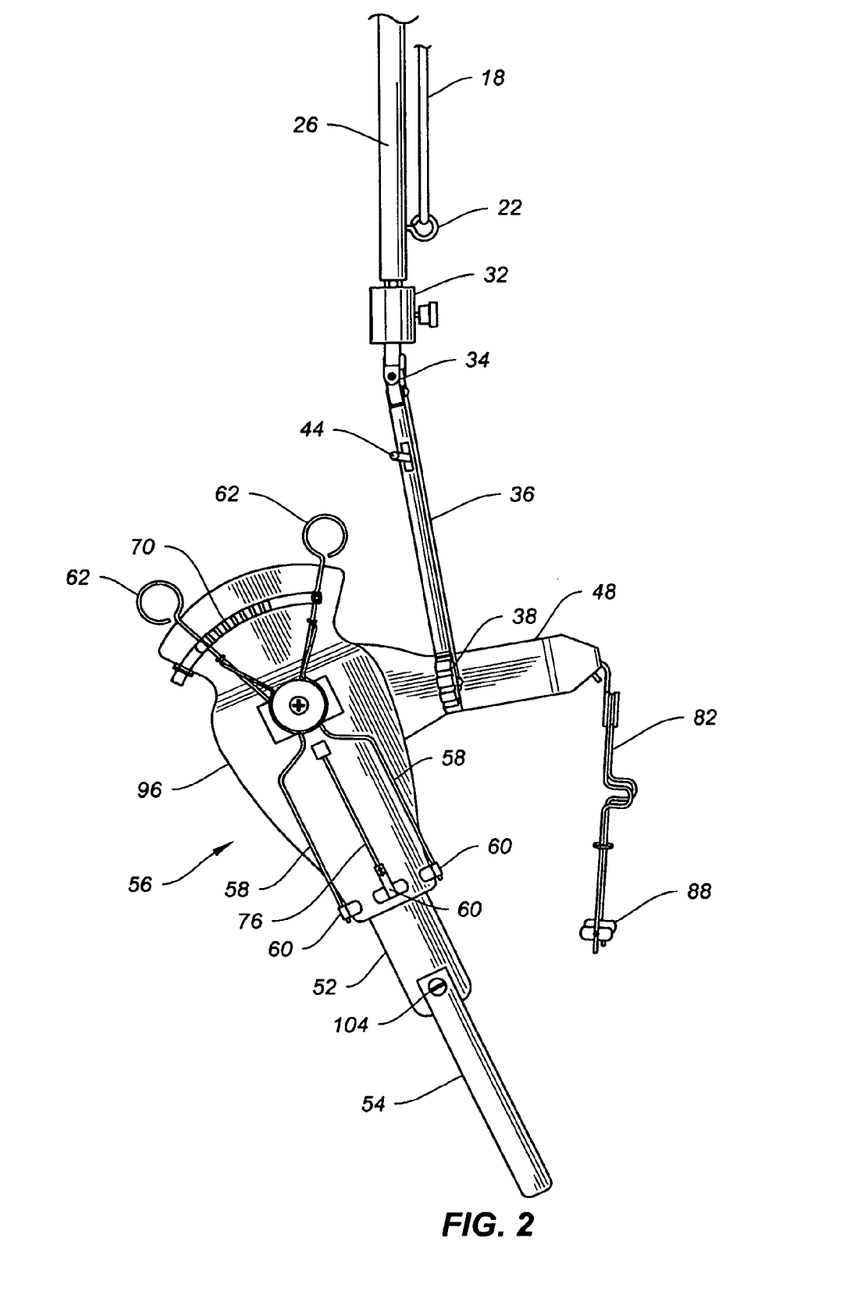
FIG. 2 is a more detailed orthogonal view of the apparatus.

FIG. 2 shows the apparatus 10 in greater detail gripping a forearm and hand in traction. It again shows the lockable swivel 32 and a universal joint 34 affixed to the base of the rotation control rod 26, which enables the elongate adjustable suspension arm 36 and its attached apparatus 10 to rotate freely until locked, enabling the positioning of the forearm in varying degrees of supination or pronation, and to be then locked in that position. It also illustrates the finger gripping device 56 with its component parts, and the thumb traction device 82 and its component parts. The finger gripping device 56 is suspended by the elongate adjustable suspension arm 36 which is rotatable around sprocket 38, which is mounted on the outrigger arm 48 and controlled by trigger 44.

The finger gripping device 56 comprises a an elongate base plate 96, a an adjustable elongate palmar tail plate 52 and a volar forearm pressure blade 54 rotatably attached to it by fastener 104. The cantilever spring blades 58 and the plurality of soft-surfaced crescent shaped segments 60 can be closed towards each other, as with scissors, to grip the base of the index and long fingers by means of the eye rings 62 and the locking ratchet 70. The thumb traction device 82 and its thumb grips 88 are described in detail in FIG. 3.

In a preferred embodiment, the elongate cantilever spring 76 is positioned on the elongate base plate 96 so that the soft-surfaced crescent shaped segments finger grips 60 are positioned between those of the cantilever spring blades 58, and between the bases of the index and long fingers. Together with the soft-surfaced crescent shaped segments 60 of cantilever spring blades 58, they provide the grip to the base of the index and long fingers. The elongate cantilever spring 76 insures that the grip on the fingers is uniform and similar.

Figure 8:
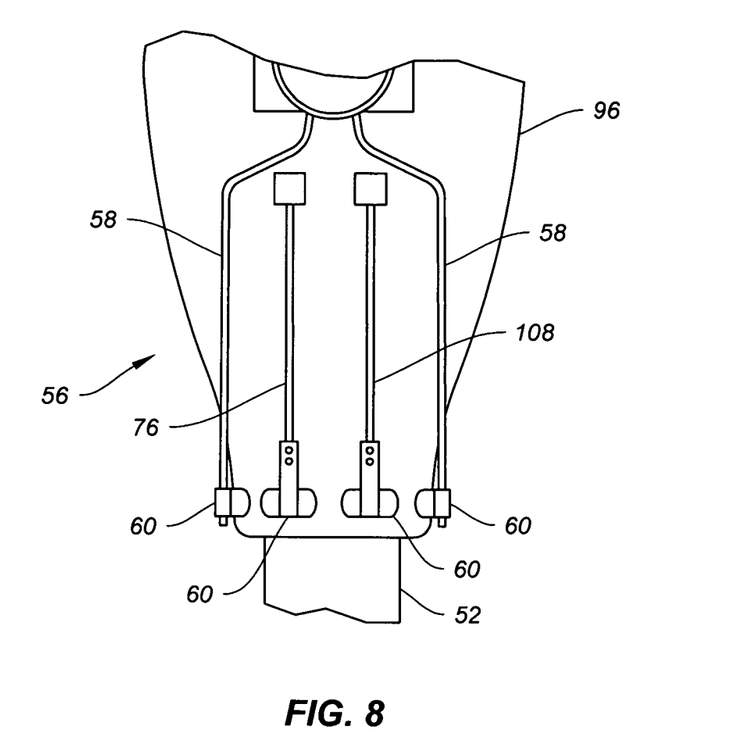
FIG. 8 shows an alternative embodiment with an additional cantilever spring for gripping three fingers.

In an alternative embodiment shown in FIG. 8, an additional elongate cantilever spring similar in all respects to spring 76 is positioned parallel to it so that its finger grips are positioned between the base of the middle and ring fingers. As a result, traction can be applied to three fingers instead of two, the index, long and ring fingers.

Figure 3:
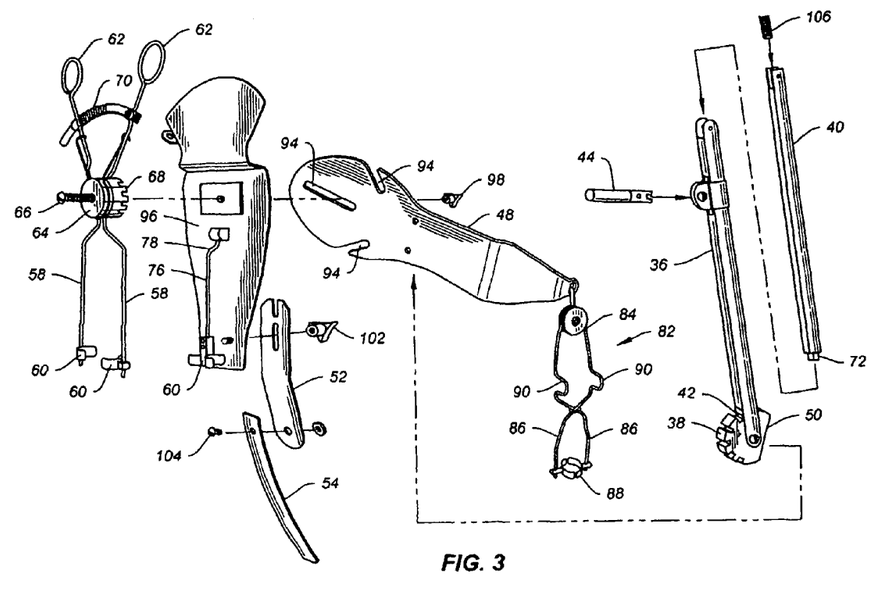
FIG. 3 is an exploded view of the apparatus.

FIG. 3 is an exploded view of the apparatus 10. The elongate adjustable suspension arm 36 comprises two ends, a first end fastened to the universal joint 34 and a second end rotatably fastened to a sprocket 38. It comprises a compression spring 106, which compels shaft 40 with a locking tooth 42 at its lower end to engage with sprocket 38 and to prevent the rotation of the suspension control arm on the sprocket until the tooth is released by the trigger 44.

The spocket 38 is approximately semicircular with the flattened and beveled edge 50 affixed to the elongate outrigger extension arm 48 of the apparatus 10. The location of the sprocket on the elongate outrigger extension arm 48 enables traction on the elongate adjustable suspension arm 36 to exert a greater traction force directed towards the thumb side of the hand, rather than towards the ulnar side, thereby resulting in an ulnar deviation, a requirement for proper positioning of the fractured wrist.

The location of the locking tooth 42 on the sprocket 38 can be varied by unlocking the tooth from the sprocket by means of trigger 44. This enables the elongate adjustable suspension arm 36 to be positioned either parallel to the apparatus elongate base plate 96 of the apparatus 10 or at an angle to it, the amount of the angle depending on the location on the sprocket selected.

Figure 4:
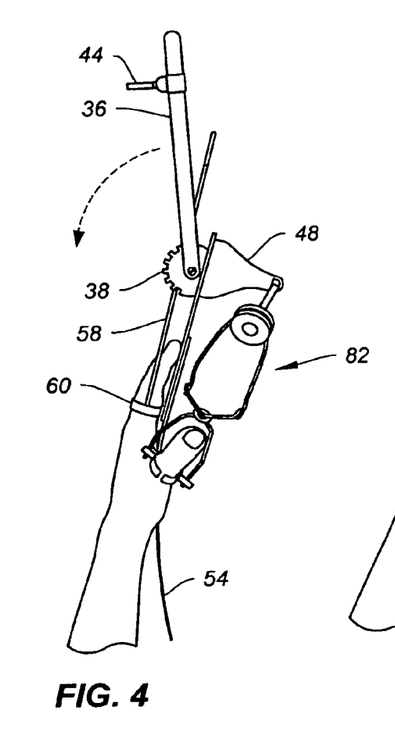
FIG. 4 is a lateral view of the forearm and hand in straight traction, without volar forearm pressure from the volar forearm pressure blade.

When the elongate adjustable suspension arm 36 is essentially parallel to the elongate base as shown in FIG. 4, the traction vector force is applied to a fully extended wrist and forearm, but when the elongate adjustable suspension arm 36 is placed at, for example, a ninety degree angle to the longitudinal axis of the elongate base, the traction vector force tends to flex the wrist, which, in conjunction with the adjustable elongate palmar tail plate 52 and the semi-flexible volar forearm pressure blade 54 produces a diffuse pressure over the volar surface of the distal radial shaft, causing the wrist and the forearm to assume the position most conducive for stability of a fractured fragment of the distal radius. The elongate palmar tail plate 52 is adjustable for various sized hands and is locked in place with a clamping knob 2, 102.

Also illustrated is the semi flexible volar forearm pressure blade 54. The blade is rotatably affixed to the elongate palmar tail plate 52 by means of a fastener 104, and can be rotated horizontally to the side, out of the way, during fracture reduction manipulation. In one embodiment the volar forearm pressure blade comprises spring metal of appropriate thickness and flexibility, but other materials such as, but not limited to, carbon fiber composites with graduated stiffness or flexibility could be used.

An important feature of the apparatus is that the adjustable elongate palmar tail plate 52 and the volar forearm pressure blade 54 conform closely to the palm of the hand and the volar surface of the forearm when the wrist is flexed, enabling a cast to be applied closely to the forearm.

This feature permits the entire apparatus to be slipped out easily from beneath the cast after the cast has hardened. This also enables the closely fitting cast to be applied without interference from bulky pressure brackets as in some prior art, so that any tendency for the fracture to re-displace while in the cast is minimized.

FIG. 3 also illustrates the elongate outrigger extension 48 and the slots 92 and 94 that engage with studs (not shown) on the back of the base plate 96 permitting it to rotate on the central pivot 66 for use with right or left injured forearms. It is then locked in place with clamping knob 1, 98.

As a result of the foregoing functions of the apparatus 10, the forearm wrist and hand can be placed in a state of traction, ulnar deviation, pronation and flexion. The apparent flexion of the wrist results from palmar pressure, and pressure over the volar distal radius combined with traction, and is not solely a flexion of the wrist joint itself, which if excessive, can result in backward displacement of the distal radial fragments.

The apparatus 10 can then be locked in this position, leaving the operators hands free to apply a proper closely fitting, well molded cast holding the fracture in as stable a position as can possibly be attained.

The FIGS. 1 to 3 also illustrates the fracture apparatus 10 employing a method of gripping the base of the fingers and thumb for the application of traction, that is not anticipated in the prior art.

Whereas the bulk of the prior art employs finger traps that are time consuming to apply and remove, and can damage the integument of the fingers, the finger gripping device 56 comprises elongate cantilever spring blades 58 with soft-surfaced crescent shaped segments 60 at the tips of the scissor shaped blades and actuatable eye-rings 62 at the opposite ends. The central axis of the spring blades holding them in place comprises rotatable discs 64, which are rotatably affixed by means of a central threaded pivot 66 and a lock washer 68 to the elongate base plate 96, of the traction apparatus 10 and are able to be releasably locked in any amount of gripping pressure by means of a locking ratchet 70.

FIG. 3 also illustrates as in FIG. 2, an individual elongate cantilever spring 76 is positioned between the cantilever spring blades 58 of the finger gripping device 56, with the first end of the individual elongate cantilever spring 78 affixed to the elongate base plate 96, and the second end comprising soft-surfaced crescent shaped segments 60 that are positioned between the bases of the index and middle fingers. The long cantilever spring 76, and its soft-surfaced crescent shaped segments 60 together with the pressure from the cantilever spring blades 58 on the bases of the radial side of the index finger and the ulnar side of the middle finger assures an even and equal finger gripping pressure on the bases of both the index and middle fingers.

This provides a means for applying traction to two fingers, the index and middle fingers as well as the thumb. It should be noted that the long cantilever springs provide a uniform pressure that constantly adjusts to the contours of the fingers, unlike rigid clamps or finger traps that have no resilience and can damage the finger.

The outer end of the elongate outrigger extension 48 comprises a device for thumb traction 82 which comprises a coil spring 84 with the elongate free ends of the coil spring 86 crossed to enable compression between the tips of the free ends of the coil springs. Soft-surfaced thumb grips 88 are located at the tips of the free ends of the coil spring which grip the base of the thumb, enabling traction to be applied to the thumb, and thus tending to deviate the wrist towards the ulnar side of the hand. An offset 90 in the free ends of the spring ends at their mid-point enables an efficient pinch grip to apply and release the device from the thumb.

FIG. 4 is a lateral view of a hand in straight traction in the fracture apparatus 10. It illustrates the elongate adjustable suspension arm 36 having been released by trigger 44 and rotated on the sprocket 38 so that it is almost vertical with respect to the hand and forearm, thus enabling manipulative reduction of the fracture.

The forearm pressure blade 54 is positioned some distance away from the volar surface of the forearm and is not applying pressure to the forearm. It can also be rotated to the side and out of the way during manipulation of the fracture. The cantilever spring blades 58 and 76, and the thumb traction device 82, are applying traction to the forearm.

Figure 5:
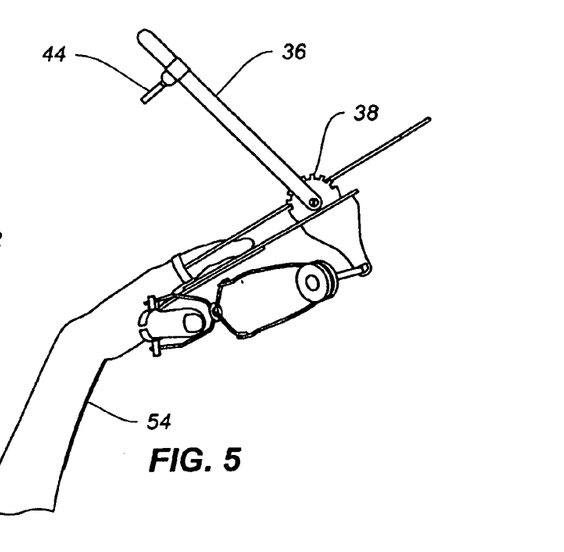
FIG. 5 is a lateral view of the wrist and hand in traction with the wrist flexed and pressure being applied to the volar forearm by the volar forearm pressure blade of the apparatus.

FIG. 5 is a lateral view of the hand and forearm in traction after manipulative reduction of the fracture has taken place. It shows the elongate adjustable suspension arm 36 to be rotated on the sprocket 38 causing the traction vector force acting on the palmar tail plate 52 (not shown) and the volar forearm pressure blade 54 to press against the volar surface of the palm of the hand and the volar surface of the distal forearm resulting in flexion of the wrist, which when combined with padded cast pressure over the dorsal surface of the distal radius, assures stability of the distal radial fracture fragments.

FIG. 6 illustrates the pulleys 14 and 15 and the pulley bracket 28 with a square opening 100 that enables the rotation control rod 26 to translate through the opening, but prevents its rotation in the opening. This feature together with the lockable swivel 32 enables the forearm to be positioned in supination or pronation and locked in place. A hairpin cotter pin 30 limits the translation of the rotation control rod in the opening of the bracket.

Figure 7:
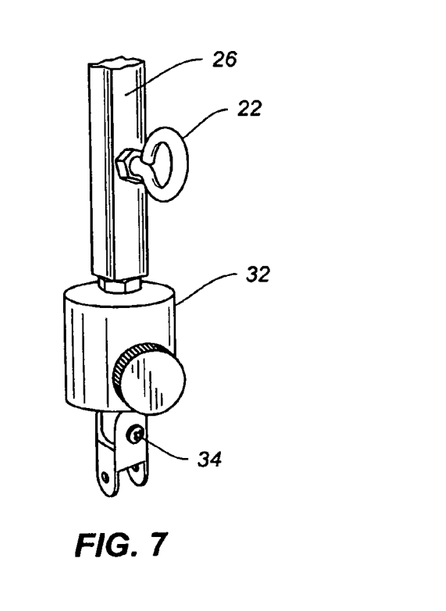
FIG. 7 is a view of the lockable swivel, and the universal joint.

FIG. 7 illustrates the lockable swivel 32 attached to the rotation control rod 26, and the universal joint 34, that enables the hand and forearm to be placed into any amount of supination or pronation, and for it to be locked in that position. Also shown is the eyelet 22 for the attachment of a traction rope or cable.

FIG. 8 illustrates an alternative embodiment of the traction apparatus 10 wherein an additional individual elongate cantilever spring 108 is positioned between the cantilever spring blades 58 enabling the apparatus to grip three fingers.

Parts List, Apparatus for the treatment of fractures of the distal radius.

| | |
|---|---|
| 10. | Fracture Apparatus |
| 12. | Support Assembly |
| 14. | First pulley |
| 15. | Second pulley |
| 16. | Weight |
| 18. | Elongate flexible support means |
| 20. | Restraining cuff |
| 22. | Eyelet |
| 24. | First support bar |
| 25. | Second support bar |
| 26. | Rotation control rod |
| 28. | Pulley bracket |
| 30. | Hairpin cotterpin |
| 32. | Lockable swivel |
| 34. | Universal joint |
| 36. | Elongate adjustable suspension arm |
| 38. | Sprocket |
| 40. | Elongate internal shaft |
| 42. | Locking tooth |
| 44. | Trigger |
| 48. | Elongate outrigger extension |
| 50. | Beveled and flattened edge |
| 52. | Elongate palmar tail plate |
| 54. | Volar forearm pressure bade |
| 56. | Finger gripping device |
| 58. | Cantilever spring blades |

-continued

Parts List, Apparatus for the treatment of fractures of the distal radius.

| | |
|---|---|
| 60. | Soft-surfaced crescent shaped segments |
| 62. | Eye rings |
| 64. | Rotatable discs |
| 66. | Central threaded pivot |
| 68. | Lock washer |
| 70. | Ratchet |
| 76. | Individual cantilever spring |
| 78. | Proximal end of cantilever spring |
| 82. | Thumb traction device |
| 84. | Flat coil spring |
| 86. | Tips of coil spring |
| 88. | Soft surfaced thumb grips |
| 90. | Offset pinch grip |
| 94. | Slots |
| 96. | Elongate base plate |
| 98. | Second Clamping knob |
| 100. | Square opening |
| 102. | First Clamping knob |
| 104. | Fastener |
| 106. | Compression spring |
| 108. | Additional Individual Cantilever spring |

What I claim is:

1. A traction apparatus for applying traction to a forearm and hand to facilitate the reduction of a fractured distal forearm and for holding the forearm and hand in an optimal position of traction, ulnar deviation, pronation and flexion following reduction of the fracture and during an application of a cast, comprising:

a support assembly, said support assembly comprising a traction tower, said traction tower comprising a vertically oriented columnar support with a first support bar across an upper end of said vertically oriented columnar support, and with said first support bar having a first end and a second end, and with said first end of said first support bar comprising a first pulley with a pulley support bracket, and with said pulley support bracket comprising an opening of predetermined shape, and with said second end of said first support bar comprising a second pulley, and with said first and second pulleys supporting an elongate flexible suspension means, said elongate flexible suspension means comprising a rope or cable, and with said elongate flexible support means comprising a first end and a second end, and with said first end of said elongate flexible suspension means attached to said traction apparatus, and with said second end of said elongate flexible suspension means attached to a variable weight, and with a second support bar spaced apart from said first support bar, said second support bar comprising a means for restraining an upper arm, said means comprising a restraining cuff, and with said traction apparatus comprising a finger gripping device, said finger gripping device comprising a plurality of soft-surfaced crescent-shaped segments positionable adjacent to a base of fingers to be placed therein, said plurality of soft-surfaced crescent-shaped segments variably tensionable towards a base of a plurality of fingers by an elongate cantilevered spring means, said elongate cantilevered spring means comprising a scissor-shaped arrangement of elongate blades with a central pivot, and with said plurality of soft-surfaced crescent-shaped segments positioned at one end of said elongate blades, and with scissor-shaped eye rings positioned at the opposite end, and with a locking ratchet between said elongate blades, and with said elongate cantilevered spring means, said locking ratchet means and said plurality of soft-surfaced crescent-shaped segments rotatably affixed to an elongate base plate, said elongate base plate comprising an elongate rigid plate with a first end and a second end, and with a centrally positioned longitudinal axis thereby enabling a compressive force directed towards a base of said fingers, and with an elongate cantilever spring means comprising a first end and a second end, and with said first end of said elongate cantilever spring affixed to said elongate base plate and with said second end of said elongate cantilever spring means comprising a plurality of soft-surfaced crescent-shaped segments, and with said elongate cantilever spring means with said soft-surfaced crescent-shaped segments positionable between a base of an index and middle fingers, enabling said base of said fingers to be compressed and gripped by means of said plurality of soft-surfaced crescent-shaped segments at said ends of said elongate blades of said scissor-shaped cantilever spring means, and with said elongate base plate comprising an elongate outrigger extension, said elongate outrigger extension comprising a first end and a second end and with a centrally positioned longitudinal axis between said first and second ends, and with said first end of said elongate outrigger extension rotatably affixed to said elongate base plate approximately midway between said first and second ends of said elongate base plate, with said longitudinal axis of said elongate outrigger extension positionable at approximately right angles to said centrally positioned longitudinal axis of said elongate base plate, and with a resulting positionability enabling the use of said traction apparatus with right or left forearms, and with said second end of said elongate outrigger extension comprising a thumb traction device loosely fastened to said second end of said elongate outrigger extension, said thumb traction device comprising soft-surfaced crescent-shaped segments positioned at approximately parallel ends of a coil spring, said coil spring providing a compressive force directed towards a base of a thumb, said compressive force enabling a base of a thumb to be gripped, and with said approximately parallel ends of said coil spring comprising offsets at a mid\-point of said approximately parallel ends, said offsets comprising pinch grips, and with said elongate outrigger extension also comprising an elongate adjustable suspension arm, said elongate adjustable suspension arm comprising an elongate tubular rod with a first end and a second end, and with said first end rotatably fastened to a toothed sprocket, said toothed sprocket comprising a toothed disc with a truncated flattened edge and a central opening, and with said truncated flattened edge of said toothed sprocket fixed to said elongate outrigger extension at a location approximately mid-way between said first end and said second end of said elongate outrigger extension, thereby enabling a traction force directed from said location to cause a wrist to be deviated toward an ulnar side of said wrist, and with said elongate adjustable suspension arm also comprising an internal shaft with a spring-loaded tooth, said spring-loaded tooth positioned at said first end of said elongate suspension arm and with said spring-loaded tooth enabling said elongate adjustable suspension arm to engage with said toothed sprocket, thereby enabling a changing and variation of a position of said elongate adjustable suspension arm on said toothed sprocket, thereby enabling a fractured wrist to be positioned and held in varying degrees of flexion while in traction, and with said second end of said elongate adjustable suspension arm comprising a trigger means, said trigger means enabling said spring-loaded tooth to engage or disengage with said toothed sprocket, and with said second end of said elongate adjustable suspension arm fastened to a locking swivel by means of a universal joint, said locking swivel enabling rotation of said elongate adjustable suspension arm relative to an attached elongate non-rotatable rotation control rod, and with said rotation control rod comprising an elongate rod with a square cross-section, and with said non-rotatable rotation control rod comprising a first end and a second end, and with said first end of said rotation control rod rigidly attached to said locking swivel, and with said first end of said rotation control rod also comprising a means for the attachment of said elongate flexible suspension means such as a rope or cable, said means for attachment comprising an eyelet, and with said second end of said rotation control rod positioned within said opening of predetermined shape in said pulley support bracket, and with said pulley support bracket enabling translation but not rotation of said rotation control rod in said opening of predetermined shape in said pulley support bracket, thereby enabling a forearm to be positioned and held in an optimal position of pronation, and with said elongate flexible suspension means extending from said attachment to said first end of said rotation control rod, through said first pulley and through said second pulley to a variable weight, and with a palmar tail plate, said palmar tail plate comprising a rigid elongate plate with a first end and a second end, and with the said first end of said palmar tail plate slidingly and lockably attached to said first end of said elongate base plate by means of a clamping knob, said palmar tail plate slightly curved and adjustable enabling said palmar tail plate to conform to a palmar surface of a hand, and with a volar forearm pressure blade, said volar forearm pressure blade comprising an elongate semi-flexible blade means, a first end and a second end, and with said first end of said volar forearm pressure blade rotatably attached to said second end of said palmar tail plate, said volar forearm pressure blade enabling diffuse pressure to be exerted on a volar surface of a distal forearm, with a resulting flexion of a wrist area, whereby said traction apparatus enables the reduction of fractures of a distal radius and holds a forearm and wrist in the optimal position of traction, flexion, pronation, and ulnar deviation, thereby enabling the application of a closely fitting cast.

2. The apparatus of claim 1 wherein the volar forearm pressure blade is comprised of a material such as spring steel, oriented carbon fiber composite material, or other material of suitable flexibility, stiffness and lack of surface friction, including those coated with a low friction material.

3. The apparatus of claim 1 wherein the soft surface of the crescent shaped segments for gripping the fingers is comprised of soft vinyl or similar soft coating or sleeve material.

4. The apparatus of claim 1 wherein said finger gripping device also comprises an additional elongate inter-digital cantilever spring means with said additional elongate inter-digital cantilever spring means comprising a first end and a second end, and with said first end affixed to said elongate base plate, and with said second end comprising a plurality of soft-surfaced crescent shaped segments, and with soft-surfaced crescent shaped segments
   positioned between a base of a middle and ring fingers, and with
   said additional elongate inter-digital cantilever spring means and said soft-surfaced crescent shaped segments enabling the gripping of a base of three fingers.

5. A method for treating fractures of a distal radius comprising the steps of:
   a. utilizing a traction apparatus for applying traction to a forearm and hand to facilitate the reduction of a fractured distal forearm and for holding the forearm and hand in an optimal position of traction, ulnar deviation, pronation and flexion following reduction of a fracture and during an application of a cast, comprising:
   a support assembly, said support assembly comprising;
   a traction tower, said traction tower comprising a vertically oriented columnar support with a first support bar across an upper end of said vertically oriented columnar support, and with said first support bar having a first end and a second end,
   and with said first end of said first support bar comprising a first pulley with a
   pulley support bracket, and with said pulley support bracket comprising
   an opening of predetermined shape, and with
   aid second end of said first support bar comprising a second pulley, and with said first and second pulleys supporting an elongate flexible suspension means, said
   elongate flexible suspension means comprising a rope or cable, and with said elongate flexible support means comprising a first end and a second end, and with said
   first end of said elongate flexible suspension means attached to said traction apparatus, and with said
   second end of said elongate flexible suspension means attached to a variable weight, and with a second support bar spaced apart from said first support bar, said second support bar comprising a means for restraining an upper arm, said means comprising a restraining cuff, and
   with said traction apparatus comprising a finger gripping device,
   b. positioning the fingers and thumb in said finger gripping device, said finger gripping device comprising a plurality of soft-surfaced crescent-shaped segments positionable adjacent to a base of fingers to be placed therein, said plurality of soft-surfaced crescent-shaped segments variably tensionable towards a base of a plurality of fingers by an elongate cantilevered spring means,
   said elongate cantilevered spring means comprising a scissor shaped arrangement of elongate blades with a central pivot, and with said
   plurality of soft-surfaced crescent-shaped segments positioned at one end of said elongate blades, and with
   scissor-shaped eye rings positioned at the opposite ends, and with a locking ratchet between said elongate blades, and with
   said elongate cantilevered spring means, said locking ratchet means and said plurality of soft-surfaced crescent-shaped segments rotatably affixed to a an elongate base plate, said elongate base plate comprising an elongate rigid plate with a first end and a second end, and with a centrally positioned longitudinal axis and with
   an elongate inter-digital cantilever spring means comprising a first end and a second end, and with said first end of said elongate inter-digital cantilever spring means affixed to said elongate base plate and with said second end of said additional elongate cantilever spring means comprising a plurality of soft-surfaced crescent-shaped segments, and with said elongate cantilever spring means with
   said soft-surfaced crescent-shaped segments positionable between a base of an index and middle fingers, enabling said base of said fingers to be compressed and gripped by means of said plurality of soft-surfaced crescent-shaped segments at said ends of said elongate blades of said scissor shaped cantilever spring means, and with
   said elongate base plate comprising an elongate outrigger extension, said elongate outrigger extension comprising a first end and a second end and with a centrally positioned longitudinal axis between said first and second ends, and with
   said first end of said elongate outrigger extension rotatably affixed to said elongate base plate approximately midway between said first end and
   said second end of said elongate base plate, with said longitudinal axis of said elongate outrigger extension positionable at approximately right angles to said centrally positioned longitudinal axis of said elongate base plate,
   and with a resulting positionability enabling the use of said traction apparatus with right or left forearms, and with said
   second end of said elongate outrigger extension comprising a thumb traction device loosely fastened to said second end of said elongate outrigger extension, said thumb traction device comprising soft-surfaced crescent-shaped segments positioned at approximately parallel ends of a coil spring, said coil spring providing a compressive force directed towards a base of a thumb, said compressive force enabling a base of a thumb to be gripped,
   and with said approximately parallel ends of said coil spring comprising offsets at a mid\-point of said approximately parallel ends, said offsets comprising pinch grips,
   and with said elongate outrigger extension also comprising an
   elongate adjustable suspension arm, said elongate adjustable suspension arm comprising an elongate tubular rod with a first end and a second end, and with said first end rotatably fastened to a toothed sprocket, said toothed sprocket comprising a toothed disc with a truncated flattened edge and a central opening, and with
   said truncated flattened edge of said toothed sprocket fixed to said elongate outrigger extension at a location approximately mid-way
   between said first end and said second end of said elongate outrigger extension, thereby enabling a traction force directed away from said location to cause a wrist to be deviated toward an ulnar side of said wrist, and with said elongate adjustable suspension arm also comprising an internal shaft with a spring-loaded tooth, said spring-loaded tooth positioned at said first end of said elongate suspension arm and with said spring-loaded tooth enabling said elongate adjustable suspension arm to engage with said toothed sprocket, thereby enabling a changing and variation of a position of said elongate adjustable suspension arm on said toothed sprocket, thereby enabling a fractured wrist to be positioned and held in varying degrees of flexion while in traction, and with said second end of said elongate adjustable suspension arm comprising a trigger means, said trigger means enabling said spring-loaded tooth to engage or disengage with said toothed sprocket, and with said second end of said elongate adjustable suspension arm fastened to a locking swivel by means of a universal joint, said locking swivel enabling rotation of said elongate adjustable suspension arm relative to an attached elongate non-rotatable rotation control rod, and with said non-rotatable control rod comprising an elongate rod with a square cross section, and with said non-rotatable rotation control rod comprising a first end and a second end, and with said first end of said rotation control rod rigidly attached to said locking swivel, and with said first end of said rotation control rod also comprising a means for the attachment of said first end of said elongate flexible suspension means such as a rope or cable, said means for attachment comprising an eyelet, and with said second end of said rotation control rod positioned within said opening of predetermined shape in a said pulley support bracket, and with said pulley support bracket enabling translation but not rotation of said rotation control rod in said opening of predetermined shape in said pulley support bracket, thereby enabling a forearm to be positioned and held in an optimal position of pronation, and with said elongate flexible suspension means extending from said attachment to said first end of said rotation control rod through said first pulley and through said second pulley to a variable weight, and with a palmar tail plate, said palmar tail plate comprising a rigid elongate plate with a first end and a second end, and with the said first end of said palmar tail plate slidingly and lockably attached to said first end of said elongate base plate by means of a clamping knob, said palmar tail plate slightly curved and adjustable enabling said palmar tail plate to conform to a palmar surface of a hand, and with a volar forearm pressure blade, said volar forearm pressure blade comprising an elongate semi-flexible blade means, a first end and a second end, and with said first end of said volar forearm pressure blade rotatably attached to said second end of said palmar tail plate, said volar forearm pressure blade enabling diffuse pressure to be exerted on a volar surface of a distal forearm, with a resulting flexion of a wrist area, c. applying counter-traction to above the elbow by means of said restraining cuff fastened to said second support bar, d. applying sufficient weight to said second end of said elongate flexible suspension means to dis-impact a fracture, e. manipulating and reducing the fracture, f. rotating said elongate adjustable suspension arm on said toothed sprocket to enable said palmar tail plate and said volar forearm pressure blade to flex and press against, and to conform to a volar curvature of a wrist and forearm, and to cause a slight flexion of a wrist, enabling a fracture to be held in place, g. rotating a hand and forearm into a position of pronation and locking said locking swivel thereby maintaining said hand and forearm in said position of pronation, h. applying a closely fitting cast, I. removing said traction apparatus with said soft-surfaced crescent-shaped segments from a thumb and fingers and sliding said palmar tail plate and said volar forearm pressure blade out from under said closely fitting cast.

6. The method of claim 5 wherein said finger gripping device also comprises an additional elongate inter-digital cantilever spring means comprising a first end and a second end, and with said first end affixed to said elongate base plate, and with said second end comprising a plurality of soft-surfaced crescent-shaped segments and with said soft-surfaced crescent-shaped segments positioned between a base of a middle and ring fingers, said additional elongate inter-digital cantilever spring means and said soft-surfaced crescent-shaped segments enabling the gripping of a base of three fingers.

* * * * *